(12) United States Patent
Koegel et al.

(10) Patent No.: US 6,326,404 B1
(45) Date of Patent: Dec. 4, 2001

(54) USE OF O-DESMETHYL-N-MONO-DESMETHYL-TRAMADOL

(75) Inventors: Babette Koegel, Langerwehe; Werner Englberger, Stoblerg; Hagen-Heinrich Hennies, Simmerath; Elmar Friderichs, Stolberg, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/642,152

(22) Filed: Aug. 21, 2000

(30) Foreign Application Priority Data

Feb. 21, 2000 (DE) .......................................... 200 02 943 U
Feb. 21, 2000 (JP) .................................................. 12-043446

(51) Int. Cl.⁷ ................................................. A61K 31/135
(52) U.S. Cl. .............................................................. 514/646
(58) Field of Search ............................................... 514/646

(56) References Cited

FOREIGN PATENT DOCUMENTS

WO 99-66919    12/1999    (WO) .

OTHER PUBLICATIONS

Lintz et al., "Metabolisms von Tramadol bei Mensch und Tier", Arzneim.—Forsch./Drug Res. 31 (II), Nr. 11 (1981), pp. 1932–1943.

Raffa et al., "Complementary and Synergistic Antinociceptive Interaction between the Enantiomers of Tramadol", Journal of Pharmacology and Experimental Therapeutics, vol. 267, No. 1., (1993), pp. 331–340.

Miyamoto et al., "Spinal coadministration of ketamine reduces the development of tolerance to visceral as well as somatic antinociception during spinal morphine infusion", Chemical Abstracts, vol. 132, No. 14, Reference 175717K, Apr. 3, 2000.

*Primary Examiner*—William R. A. Jarvis
(74) *Attorney, Agent, or Firm*—Crowell & Moring LLP

(57) ABSTRACT

This invention relates to a method of treating pain, urinary incontinence, diarrhea or pruritus using O-desmethyl-N-mono-desmethyl-tramadol.

10 Claims, 1 Drawing Sheet

Fig. 1)
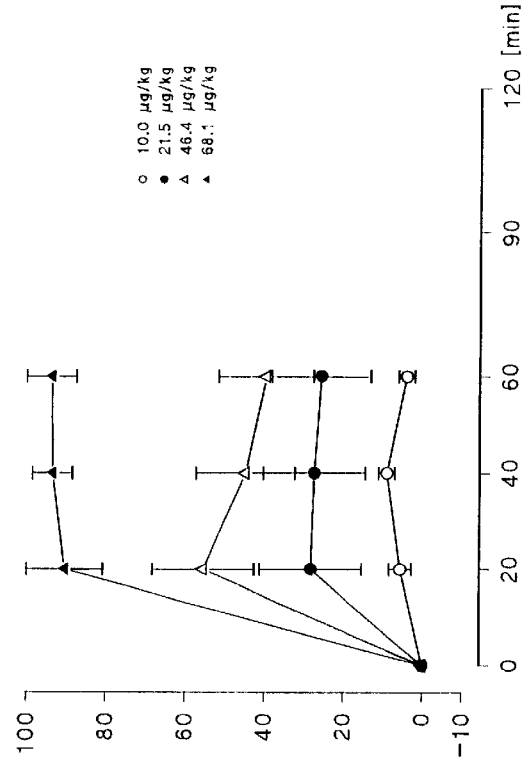
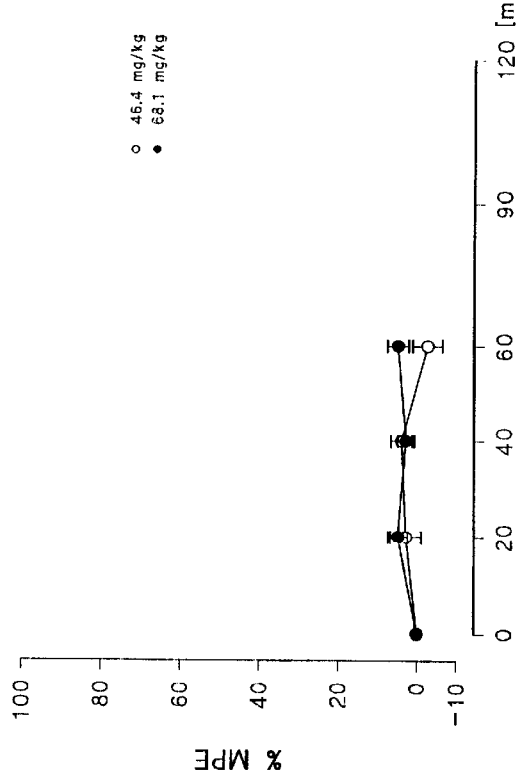

USE OF O-DESMETHYL-N-MONO-DESMETHYL-TRAMADOL

BACKGROUND OF THE INVENTION

This invention relates to the use of O-desmethyl-N-mono-desmethyl-tramadol for the production of pharmaceutical compositions for the treatment of pain and various related indications as well as pharmaceuticals comprising O-desmethyl-N-mono-desmethyl-tramadol.

The treatment of pain conditions is of great importance in medicine. There is currently a world-wide need for additional pain therapy. The pressing requirement for a target-oriented treatment of pain conditions which is right for the patient which is to be understood as the successful and satisfactory treatment of pain for the patients is documented in the large number of scientific works which have recently and over the years appeared in the field of applied analgesics or on basic research on nociception.

SUMMARY OF THE INVENTION

The underlying object of the present invention was to provide a substance useful in the treatment of pain and also related indications, as well as pharmaceutical compositions for such treatment.

It has now been found that O-desmethyl-N-mono-desmethyl-tramadol is useful in the treatment of pain and also related indications.

One main aspect of the invention is therefore the use of O-desmethyl-N-mono-desmethyl-tramadol as a racemate, a mixture of its enantiomers or a single enantiomer in the form of its base or salts of physiologically acceptable acids for the production of a pharmaceutical composition for the treatment of pain.

O-desmethyl-N-mono-desmethyl-tramadol (sometimes referred to as M5 in the literature and in the following text) is known as one of the in vivo metabolites of Tramadol (1RS,2RS)-2[(dimethylamino)methyl]-1-(3-methoxyphenyl)cyclohexanol; Lintz et al. Arzneim.-Forsch./Drug Res. 31(11), 1932–1943, 1981).

Tramadol assumes a special position amongst centrally acting analgesics. Since this active ingredient acts as a strong inhibitor of pain without the side effects which are known for opioids (J. Pharmacol. Exp. Ther. 267, 331 (1993)). Tramadol is a racemate and consists of equal amounts of (+) and (−) enantiomers. It is a centrally acting analgesic with an opiod and a non-opioid mechanism of action. The opioid properties are derived from $\mu$-opioid receptor interaction, whereas the inhibition of neuronal re-uptake of monoamines (norepinephrine (NE) and serotonin (5-HT)) is responsible for the non-opioid activity. The opioid receptor affinity of tramadol is very low, but the compound is extensively metabolized by O- and N-demethylation.

In the prior art, the metabolite M5 is not described as having analgesic properties. The recent and surprising findings of the inventors leading to this patent application were on the one hand, the fact that M5 has a strong $\mu$-opioid receptor affinity which was strong enough to induce in vivo analgesic activity as proven after direct administration into a brain ventricle, and on the other hand, the fact that M5 shows a poor penetration of the blood brain barrier or even seemed to be unable to penetrate it.

The fact that peripherally applied M5 does not—at least not noticably—act in the central nervous system (CNS) makes M5 an ideal compound for a peripheral treatment of pain avoiding any analgesic action on the CNS. Therefore the use of O-desmethyl-N-mono-desmethyl-tramadol as a racemate, a mixture of its enantiomers or as a single enantiomer in the form of its base or salts of physiologically acceptable acids for the production of a pharmaceutical composition for the peripheral treatment of pain is a preferred embodiment of this invention.

Kinds of pain which stem from a peripheral cause and/or which may be treated peripherally include inter alia burn pain, wound pain, visceral pain, soft-tissue pain, articular pain, and cancer pain, which are therefore preferred indications for the use of M5. The usefulness of M5 to treat peripheral pain is believed due to the high $\mu$-opioid receptor affinity. So another aspect of the invention is the use of O-desmethyl-N-mono-desmethyl-tramadol as a racemate, as a mixture of its enantiomers or as a single enantiomer in the form of its base or salts of physiologically acceptable acids for the production of a pharmaceutical composition for the treatment of burn pain, wound pain, visceral pain, soft-tissue pain, articular pain and/or cancer pain.

Surprisingly it was further shown that O-desmethyl-N-mono-desmethyl-tramadol is also usable for the treatment of urinary incontinence and/or pruritus and for the treatment diarrhea. These therapeutic activities may also be due to the high $\mu$-opioid receptor affinity. Therefore, a further object of the invention is the use of O-desmethyl-N-mono-desmethyl-tramadol as a racemate, a mixture of its enantiomers or a single enantiomer in the form of its base or salts of physiologically acceptable acids for the production of a pharmaceutical for the treatment of urinary incontinence, diarrhea and/or pruritus.

The racemate of M5 is very effective for the treatment in the above mentioned indications. Surprisingly, however, the (+)-enentiomer of M5 ((+)-O-desmethyl-N-mono-desmethyl-tramadol) showed a very pronounced activity as well. Therefore, a highly preferred embodiment of the invention is the use of (+)-O-desmethyl-N-mono-desmethyl-tramadol in the form of its base or salts of physiologically acceptable acids for the production of a pharmaceutical and for treatment of any of the above mentioned indications.

In some of the above-mentioned indications, especially in pain associated with burns or wounds (but with sore and itching skin as well), the skin is damaged leading to an elevated risk of infection. To prevent or treat an infection, an anti-infective agent such as an antibiotic or disinfectant such as polyvidon-iodine is used. Especially in these indications it is useful to combine antibiotics or disinfectants such as polyvidon-iodine with O-desmethyl-N-mono-desmethyl-tramadol. Therefore, another preferred aspect of the invention is the use of O-desmethyl-N-mono-desmethyl-tramadol in combination with an anti-infective agent.

Salts of physiologically acceptable acids according to this invention include both salts with inorganic and with organic acids. The hydrochloride salt is especially preferred.

A further object of the invention is to provide pharmaceutical compositions comprising O-desmethyl-N-mono-desmethyl-tramadol as a racemate, a mixture of its enantiomers or a single enantiomer in the form of its base or salts of physiologically acceptable acids as active ingredient.

Another aspect of the invention is to provide pharmaceutical compositions comprising the (+)-enantiomer of O-desmethyl-N-mono-desmethyl-tramadol in the form of its base or salts of physiologically acceptable acids as active ingredient.

As these above mentioned pharmaceutical compositions according to the invention seem to be especially useful in the above mentioned indications, another aspect of the invention is to provide pharmaceutical compositions according to the invention for the treatment of urinary incontinence, diarrhea, pruritus and/or especially pain, particularly burn pain, wound pain, visceral pain, soft tissue pain, articular pain, and/or cancer pain.

Another aspect of the invention is to provide pharmaceutical compositions which comprise in addition to O-desmethyl-N-mono-desmethyl-tramadol as a racemate, a mixture of its enantiomers, or a single enantiomer especially the (+)-enantiomer of O-desmethyl-N-mono-desmethyl-tramadol in the form of its base or salts of physiologically acceptable acids at least one additional active ingredient. This additional active ingredient can be any suitable pharmaceutical substance. A preferred additional active ingredient for the above mentioned special indications is at least one anti-infective agent, such as an antibiotic or a disinfectant like polyvidon-iodine.

In addition to O-desmethyl-N-mono-desmethyl-tramadol as a racemate, a mixture of its enantiomers, or a single enantiomer, especially the (+)-enantiomer of O-desmethyl-N-mono-desmethyl-tramadol, a pharmaceutical composition according to the invention might comprise at least one auxiliary material and/or additive especially carriers, excipients, support materials, lubricants, fillers, solvents, diluents, colorants, taste conditioners such as sugars, antioxidants, and/or binders. In the case of a suppository this might involve waxes or fatty acid esters or conserving agents, emulsifiers and/or carriers for parenteral administration. The selection of these auxiliary materials and/or additives and of the amounts to be used depends upon how the pharmaceutical composition is to be administered.

According to this invention it is preferred to avoid any action of the active ingredient or agent on the CNS. Therefore, on one hand, a topical or local application is preferred. Possible examples of this include dermal, subcutaneous, intramuscular, intra-articular, and/or intraperitoneal dosage forms, as well as pulmonal, buccal, sublingual, nasal, percutaneous, vaginal and/or rectal forms of administration. As M5 does not penetrate the blood-brain barrier, a systemic administration is possible without any action of the active ingredient or agent on the CNS. Examples of this include oral or parenteral administration, such as pulmonal, nasal, rectal and/or intravenous administration. Therefore, the pharmaceutical composition according to the invention can be adapted for topical or systemic administration, especially dermal, subcutaneous, intramuscular, intra-articular and/or intraperitoneal, pulmonal, buccal, sublingual, nasal, percutaneous, vaginal, oral, or parenteral, pulmonal, nasal, rectal and/or intravenous administration.

One of the preferred modes of administration is intra-articular. Since a local application of M5 is absorbed slowly and therefore is not rapidly transported away from the site of administration, the concentration at the site of administration remains high for a longer period of time, and a lesser overall dose thus is sufficient to achieve the desired therapeutic effect.

For the treatment of burn and/or wound pain the pharmaceutical composition according to the invention might preferably be in the form of a plaster and/or gauze which provides for occlusion (i.e., protective covering) of the burned or wounded skin.

For oral administration, preparations in the form of tablets, chewable tablets, dragees, capsules, granules, drops, juices, and syrups are suitable. Solutions, suspensions, readily reconstitutable dry preparations, and sprays are suitable inter alia for parenteral administration. Examples of suitable percutaneous forms of administration include the compounds according to the invention as a deposit in a dissolved form or in a patch, optionally with the addition of agents which promote dermal penetration. Suitable dermal application forms include inter alia an ointment, a gel, a cream, a lotion, a suspension, or an emulsion. The preferred form for rectal administration is a suppository. Therefore in preferred embodiments of the invention the pharmaceutical composition according to the invention is in the form of an ointment, a gel, a cream, a lotion, a suspension, an emulsion, a suppository, a solution, a tablet, a chewable tablet, a dragee, a capsule, granules, drops, a juice and/or a syrup.

It is within the scope of the invention to release the active compounds in a delayed manner from forms of preparations which can be administered as described above, especially orally, rectally or percutaneously. Accordingly, delayed-release or retard formulations are preferred formulations according to the invention.

The amount of active ingredient to be administered to the patient varies depending on the weight of the patient, on the manner of administration, on the indication, and on the severity of the illness. From 1 to 500 mg of the active ingredient are usually administered per kg of patient weight.

A further preferred aspect of the invention is to provide pharmaceutical compositions containing at least 0.05 to 90.0% of active ingredient.

The invention further relates to any of the already described pharmaceutical compositions in which the salt of O-desmethy.-N-mono-desmethyl-tramadol is a hydrochloride.

Furthermore, the invention relates to a method of treating urinary incontinence, diarrhea, pruritus and/or pain. The invention is especially useful to treat peripheral pain, especially burn pain, wound pain, visceral pain, soft-tissue pain, articular pain and/or cancer pain. The invention makes use of O-desmethyl-N-mono-desmethyl-tramadol as a racemate, as a mixture of its enantiomers, or as a single enantiomer in the form of its free base or of a salt with a physiologically acceptable acid.

BRIEF DESCRIPTION OF THE DRAWING

The invention will be described in further detail hereinafter with reference to standard pharmacological tests, the results of which are illustrated in the accompanying drawing figure.

FIG. 1 shows the tail-flick latency (%MPE) after intravenous (i.v.) or intracerebral (i.c.v.) administration of the M5 metabolite; n=10/dose.

EXAMPLES

The following examples are intended to illustrate the invention in further detail without restricting its scope.

The following described tests:

$\mu$-opioid (Naloxon) binding

Noradrenaline uptake

Serotonin uptake

Writhing test, and

Tail flick test are all well known in the literature and published patent applications.

Example 1

$\mu$-opioid (Naloxon) Binding

The $\mu$-opioid receptor binding was investigated in in vitro rat brain binding experiments using naloxone. In addition to M5, tramadol and the known further metabolites M1–M4 were investigated. The results are shown in table 1. M5 had an μ-opiod receptor affinity (naloxone binding) strong enough to induce in vivo analgesia.

Example 2

Noradrenaline Uptake

The inhibition of neuronal uptake of monoamines (norepinephrine; NE) was investigated in in vitro rat brain binding experiments. In addition to M5, tramadol and the known further metabolites M1–M4 were investigated. The results are shown in table 1. M5 had no pronounced effect.

Example 3

Serotonin Uptake

The inhibition of neuronal uptake of Serotonin (5-HT) was investigated in in vitro rat brain binding experiments. In addition to M5, tramadol and the known further metabolites M1–M4 were investigated. The results are shown in table 1. MS had no pronounced effect.

Example 4

Writhing Test

Analgesia was tested in vivo in the mice phenylquinone writhing test. M5 was intravenously administered. In addition to M5, tramadol and the known further metabolites M1–M4 were investigated. The results are shown in table 2. M5 had no pronounced effect after intravenous administration.

Example 5

Tail-Flick Test

Analgesia was tested in vivo in the mice tail-flick test. M5 was first intravenously administered and then directly into a brain ventricle. In addition to M5, tramadol and the known further metabolites M1–M4 were investigated. The results for i.v. administration are shown in Table 2, and for i.c.v. administration are shown in FIG. 1. M5 had no pronounced effect after being intravenously administered. However, after direct administration into a brain ventricle, a pronounced effect was seen.

TABLE 1

| Test Substance | Naloxone binding $IC_{50}$ [μM] | Noradrenalin uptake $IC_{50}$ [μM] | Serotonin uptake $IC_{50}$ [μM] |
| --- | --- | --- | --- |
| Tramadol | 19.1 | 2.8 | 3.1 |
| $M_1$ | 0.04 | 41.4 | 24.2 |
| $M_2$ | 49.1 | 4.27 | 10.4 |
| $M_3$ | 204 | 47.7 | 48.9 |
| $M_4$ | 23.9 | 103.9 | 375.0 |
| $M_5$ | 0.31 | 13.3 | 120.0 |

TABLE 2

| | Tail-Flick, mouse | | Writhing, mouse | |
| --- | --- | --- | --- | --- |
| Substance | $ED_{50}$ (mg/kg) i.v. | $Ed_{50}$ (μg/animal) i.c.v. | $ED_{50}$ (mg/kg) i.v. | $ED_{50}$ (μg/animal) i.c.v. |
| Tramadol | 13.6 | 98.0 | 6.93 | 67.3 |
| $M_1$ | 1.90 | 2.1 | 0.49 | 0.58 |
| $M_2$ | no effect | — | no effect | — |
| $M_3$ | no effect | — | no effect | — |
| $M_4$ | no effect | — | no effect | — |
| $M_5$ | no effect | 32.4 | no effect | 4.99 |

— = not tested

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of treating a condition selected from the group consisting of pain, urinary incontinence, diarrhea, and pruritus, said method comprising administering to a patient in need of such treatment an amount of O-desmethyl-N-mono-desmethyl-tramadol effective to treat said condition.

2. A method according to claim 1, wherein said condition is peripheral pain selected from the group consisting of burn pain, wound pain, visceral pain, soft-tissue pain, articular pain, and cancer pain.

3. A method according to claim 1, wherein said O-desmethyl-N-mono-desmethyl-tramadol is co-administered with an anti-infective agent.

4. A method according to claim 1, wherein said O-desmethyl-N-mono-desmethyl-tramadol is in the form of a racemic mixture.

5. A method according to claim 1, wherein said O-desmethyl-N-mono-desmethyl-tramadol is in the form of a mixture of enantiomers.

6. A method according to claim 1, wherein said O-desmethyl-N-mono-desmethyl-tramadol is in the form of a single enantiomer.

7. A method according to claim 6, wherein said single enantiomer is the (+)-enantiomer of O-desmethyl-N-mono-desmethyl-tramadol.

8. A method according to claim 1, wherein said O-desmethyl-N-mono-desmethyl-tramadol is in the form of a salt with a pharmaceutically acceptable acid.

9. A method according to claim 8, wherein said salt is a hydrochloride salt.

10. A method according to claim 1, wherein said O-desmethyl-N-mono-desmethyl-tramadol is in the form of a free base.

* * * * *